United States Patent [19]

Townsend, Jr.

[11] 4,292,689

[45] Oct. 6, 1981

[54] VISORED HAT CONSTRUCTION

[76] Inventor: Charles E. Townsend, Jr., 11 Ranch Rd., Orinda, Calif. 94563

[21] Appl. No.: 105,462

[22] Filed: Dec. 19, 1979

Related U.S. Application Data

[63] Continuation-in-part of Ser. No. 943,888, Sep. 19, 1978, abandoned, and a continuation of Ser. No. 743,749, Nov. 22, 1976, abandoned, which is a continuation-in-part of Ser. No. 585,266, Jun. 9, 1975, abandoned.

[51] Int. Cl.³ .............................................. A42B 1/18
[52] U.S. Cl. ............................................ 2/12; 2/177
[58] Field of Search .................... 2/177, 12, 200, 195, 2/175, 10

[56] References Cited

U.S. PATENT DOCUMENTS

| | | | |
|---|---|---|---|
| 2,769,308 | 11/1956 | Krasno | 2/200 U X |
| 3,585,643 | 6/1971 | Ryan | 2/177 |
| 3,811,130 | 5/1974 | Townsend, Jr. | 2/177 |
| 4,096,589 | 6/1978 | Goldstein | 2/12 |

Primary Examiner—Peter P. Nerbun

Attorney, Agent, or Firm—Townsend and Townsend

[57] ABSTRACT

A visored hat construction comprising an outwardly projecting substantially planar visor portion of predetermined substantial thickness formed generally in an open cell configuration. The thickness of the visor, the cell size and the angles of the cells in reference to the plane of the flat visor are correlated to substantially prevent penetration of direct sun rays through the visor to the eyes of the user. The visor and its associated hat band components for encircling the head of the user coact to provide sufficient structural integrity and strength to maintain the components in flat coplanar relationship during normal wear. The visored hat provides unobstructed lateral vision, minimal wind resistance and numerous other features. Additionally, a novel headband of sinusoidal configuration and formed of soft textured, relatively non-absorbent foam material is described with its attendant advantages of neither inducing or absorbing perspiration and providing large air ventilating openings between the headband and its spaced points of contact particularly around the user's forehead.

9 Claims, 11 Drawing Figures

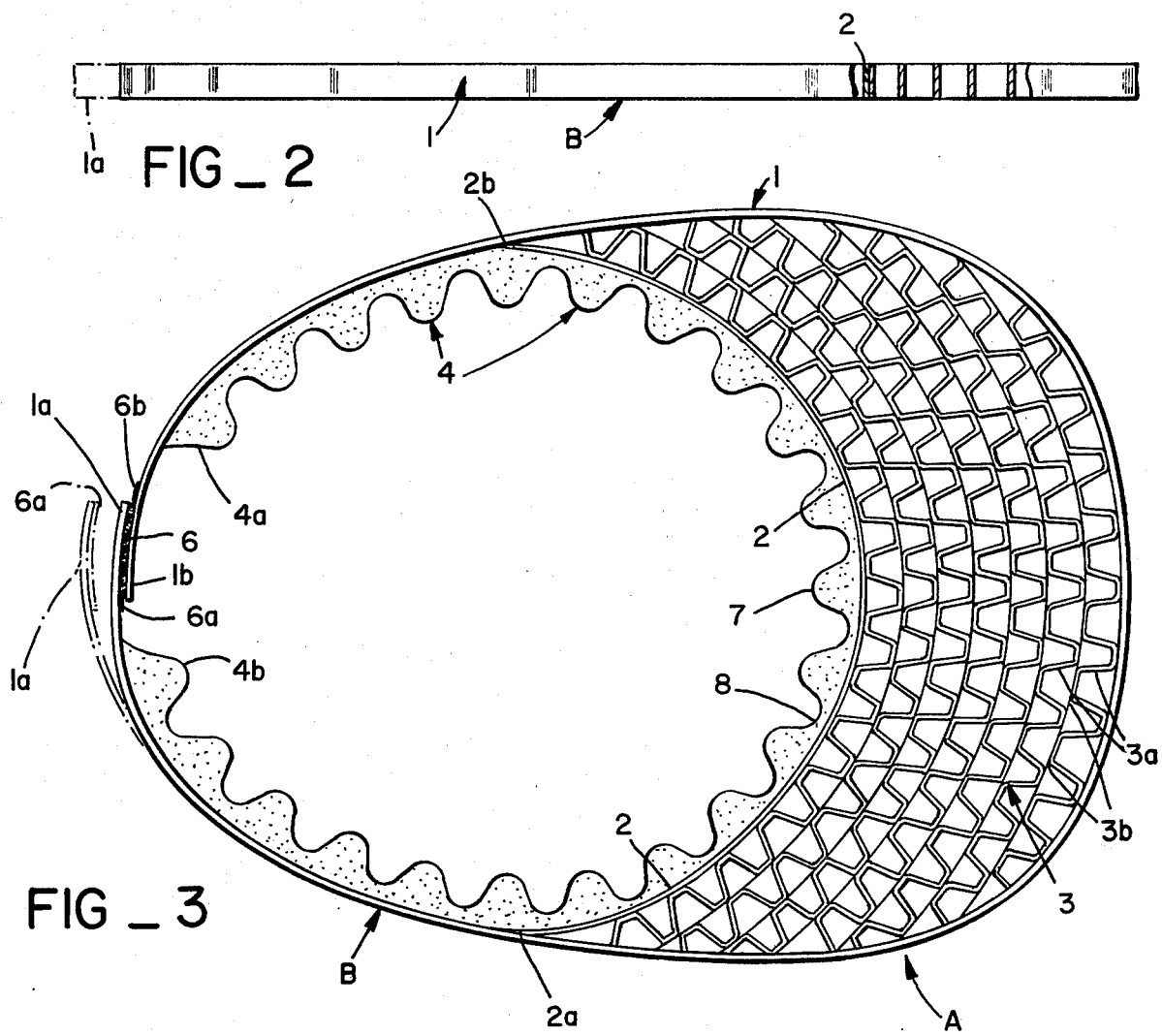
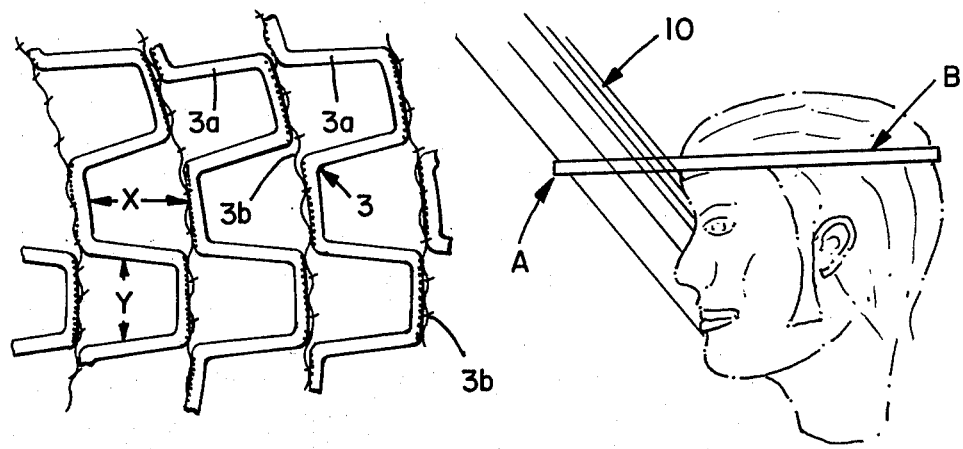

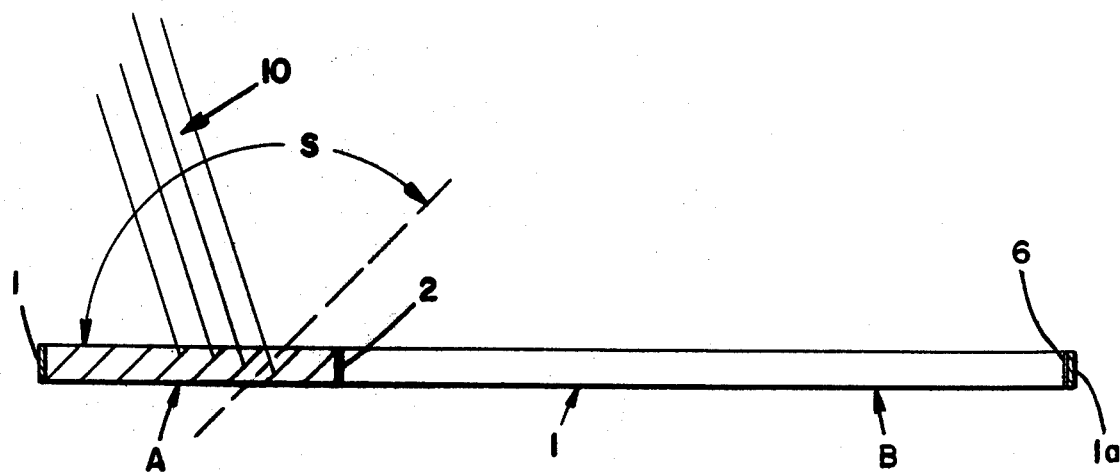
FIG_5
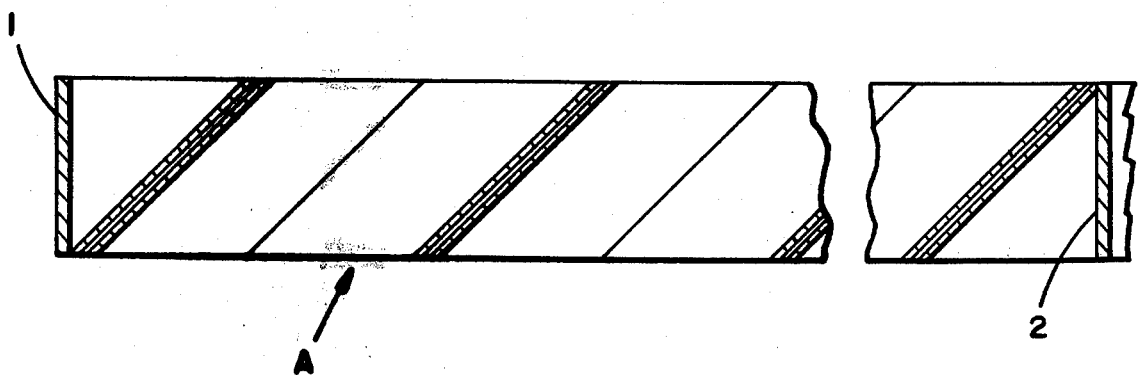
FIG_6

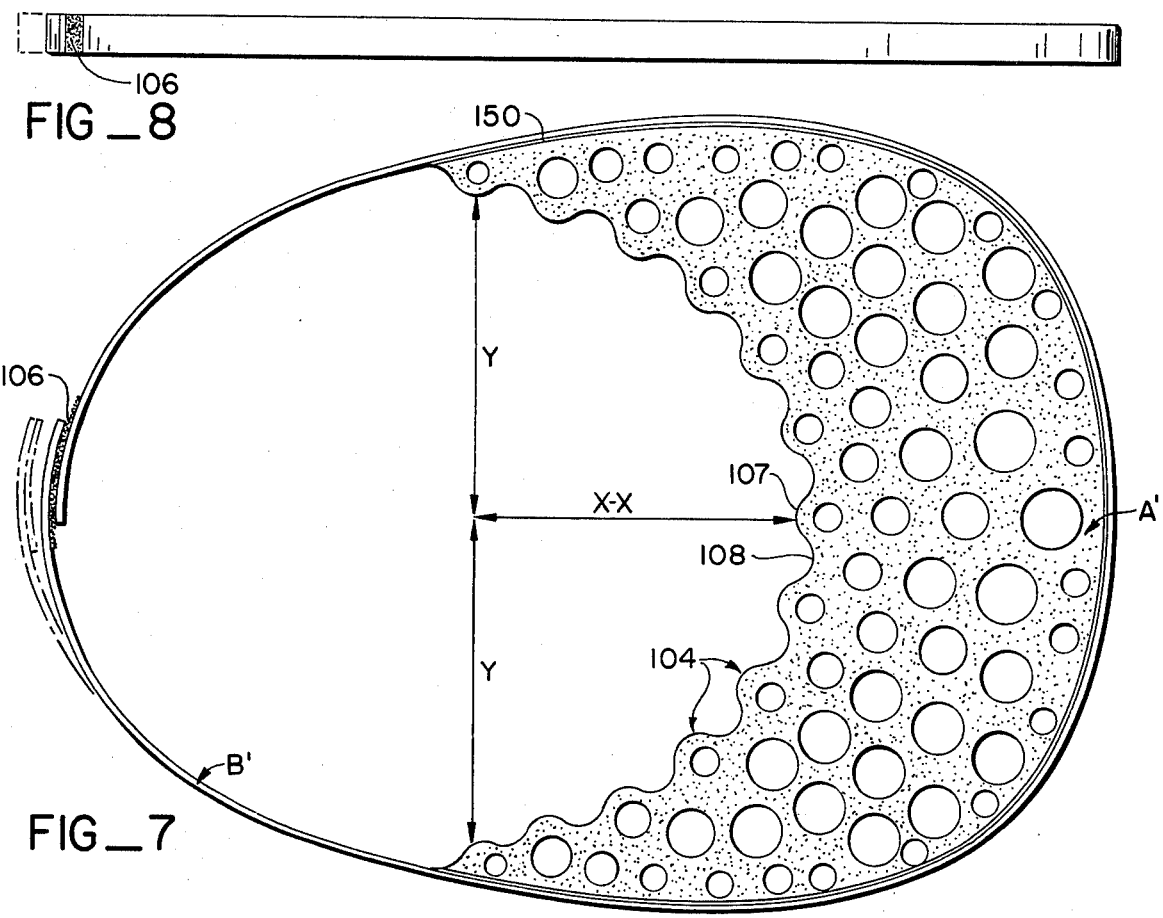
FIG_8
FIG_7
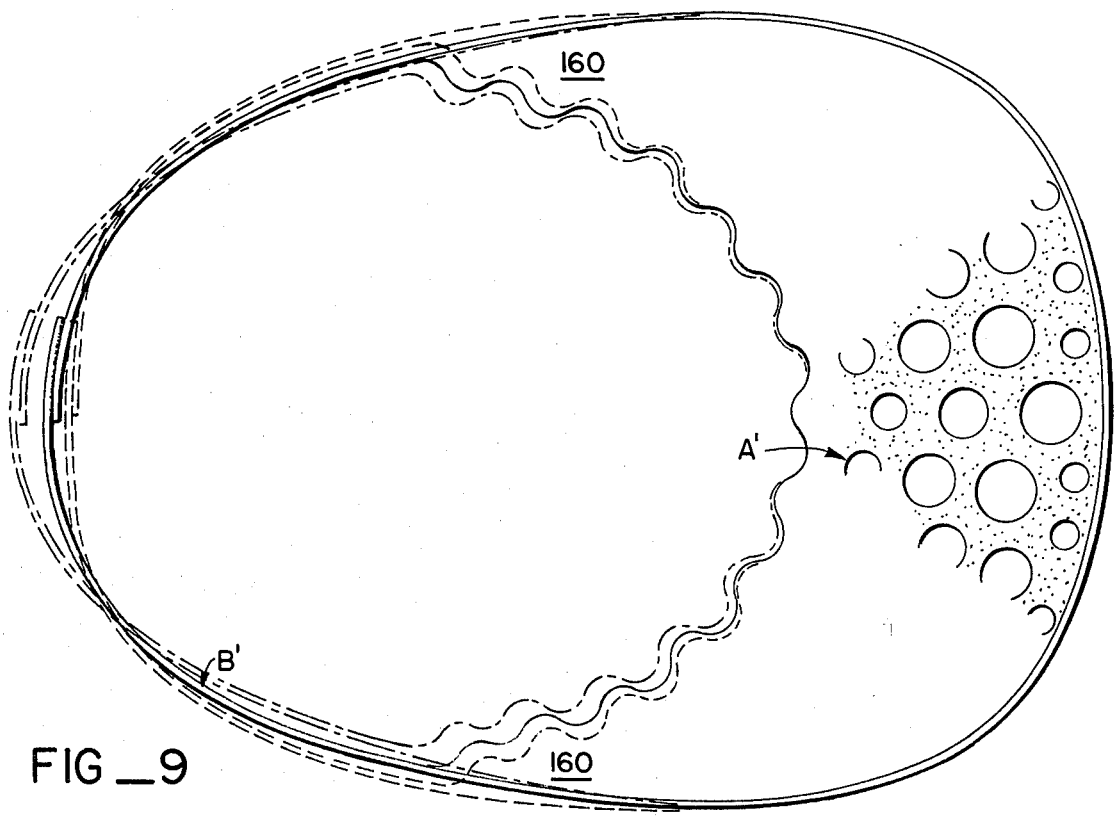
FIG_9

VISORED HAT CONSTRUCTION

This application is a continuation application of my previous patent application of the same title, Ser. No. 743,749, filed Nov. 22, 1976, now abandoned which is in turn a continuation-in-part application of application Ser. No. 585,266 filed June 9, 1975, now abandoned, and also a continuation-in-part of application Ser. No. 943,888, filed Sept. 19, 1978 and also herewith abandoned.

This invention relates to a new and improved visored hat which, in its basic form, may be constructed without any crown portion, but which in other modified forms may be made with the crown portion of any desired design, style or construction without having to modify to any substantial degree the basic combination of elements which is the subject of the present invention.

The combination of elements comprising the present invention functions to provide each and all of the following features, advantages and objectives. Briefly stated, these combined features, advantages and objectives are as follows:

Firstly, because the visor portion of the hat is made in the form of a light weight open cellular configuration, a hat with a relatively large effective sun shade area may be made extremely light weight, and, in the preferred embodiments, is on the order of five (5) to ten (10) times lighter than the more conventional cotton or light weight visored sports hats in common use today.

Secondly, and because in the preferred embodiment of the invention the projecting visor is substantially planar or flat, (as distinguished from the arched or curved visors of more conventional sports caps), the wearer has virtually total and unobstructed lateral vision.

Thirdly, because of the open cellular visor construction of the present invention, the same offers relatively little wind resistance as compared to the non-cellular cloth or plastic conventional sports caps. In any outdoor sports activity such as tennis, golf, yachting, skiing, or the like, the conventional visored sports cap is quite susceptible to being dislodged and blown off the head of the user by virtue of the resistance it offers to wind or air currents of any substantial degree or force. Basically, the usual remedy available to the wearer of a conventional visored hat to keep it from blowing off is to uncomfortably tighten the hat band around his head (assuming that it is adjustable) or to pull the hat further down over the head to make it fit tighter and to hopefully secure it against the wind forces tending to blow it off. In the present invention the open cell construction of the visor offers comparatively speaking much less wind resistance, and it is therefore usually unnecessary for the wearer either to uncomfortably tighten the hat band or to uncomfortably pull the hat down over the head to secure it in place. I have found that a hat of the present type, when adjusted to fit properly on the head will maintain itself against dislodgement under rather even vigorous conditions merely by the weight of the hat resting lightly on the cushiony contact surfaces of the head band engaging the head of the wearer.

Fourthly, although the thickness of the cellular visor, the nominal diameter of the cells or openings and the angular orientation of the cells are related in such a manner as to provide a direct sun ray or light cut-off angle to provide virtually complete shading of the eyes from the direct rays of the sun over the head, the open cells permit a filtered or lattice type of sun ray penetration to the face of the wearer, which is a feature not provided by the opaque or solid type visor of conventional sports caps. Stated otherwise, although the cellular construction of the present visor is specifically designed to protect the eyes of a wearer against direct rays of sunlight, sun rays do "filter" through the cells on the cheeks, nose and lower portions of the wearer's face which cosmetically, at least, provides a feature and advantage not provided by conventional opaque visored hats. This feature in conjunction with the preferred inner headband portion of the present hat (to be described hereinafter) permits the user to wear a visor of the present design in prolonged periods of sunlight without creating telltale lines of sunburned or suntanned areas on or across the wearer's face.

Fifthly, there is provided a novel headband which is constructed to form a sinusoidal inner surface defining inwardly projecting nodes and alternate grooves, whereby when the hat is properly adjusted to fit lightly and comfortably on the head of the wearer, the weight of the hat is supported on the head principally at the points where the nodes gently rest upon and contact adjacent portions of the wearer's head particularly the forehead. The sinusoidally formed headband is made of a relatively soft, non-absorbent, soft textured, foam plastic material, which provides still further features and advantages not found in conventional sports caps of a type that are normally provided with absorbent cloth sweat bands that substantially completely encircle and maintain continuous and uninterrupted contact with the wearer's head. These cloth sweat bands, especially during their wear in hot weather or during the play of sports such as tennis, induce and absorb perspiration, become wet and uncomfortable during wear, and rather quickly become perspiration stained which eventually dictates that the entire hat be thrown away as unsightly or at least in some way to be washed or cleaned. Utilizing the sinusoidally curved substantially non-absorbent, soft textured, foam plastic headband of the present invention eliminates entirely or minimizes to a great degree the aforesaid attendant disadvantages of the conventional absorbent cloth sweat band type of construction. More specifically, because the hat is supported only at relatively widely spaced and specific contact points around the user's head, and because the material is substantially non-absorbent, there is eliminated the continuous sweat band type structure which induces perspiration. Further, because the foam material is substantially non-absorbent there is no substantial tendency for the headband to absorb perspiration and become perspiration stained. Whatever dirt, grime, or grit that eventually becomes deposited on the foam plastic headband over a period of time can generally be easily and conveniently cleaned by wiping or brushing the outer surfaces of the headband with a mild soap and water solution.

Sixthly, the visored hat construction embodying the present invention can be made adjustable as to hat size to fit the majority of heads thereby making it feasible to economically produce either only one, or a limited few number of hat sizes to adjustably fit all normal child and adult head sizes as for example, from about $6\frac{1}{2}$ to $7\frac{3}{4}$ hat sizes.

In one embodiment of the invention which will be described in detail hereinafter, the visor part of the cap is formed from a single integral flat section or sheet of a very low density and light weight substantially opaque and non-flective cushiony plastic foam material such as 2 lb./cu.ft. density cross-linked polyethylene foam. In the manufacturing process relatively large sheets of the foam material of predetermined thickness (preferably $\frac{3}{8}''$ thick) are die cut, and in a single operation the shape of the visor as well as the headband portion thereof is defined together with the multiple openings or "cells" which extend through the thickness of the hat. In this embodiment approximately 80 circular holes are formed throughout the surface area of the visor which gives the visor a generally honeycomb type cellular configuration with the size of the holes being related to the thickness of the foam material to provide proper light cutoff angles for protecting the eyes against direct sunlight while at the same time rendering the visor with a sufficient amount of open area to make the visor relatively wind resistant. Further, by cutting out the 80 plus holes in the material the weight of the visor is and can be greatly reduced. In this embodiment a $\frac{3}{8}''$ thick flat section of 2 lb./cu.ft. cross-linked polyethylene foam provided with a hole pattern as hereinafter described, and with attached hat band, can be made to weigh approximately 7 grams or 0.25 ounces in total weight. A conventional cloth open top tennis visor in popular use today weighs 1½–2 ounces and because of its propensity to absorb perspiration and become damp or wet, the weight of the moistened cloth hat can very substantially increase from its original dry weight during wear.

More specific reference is now had to the accompanying drawings in which the same numbers represent corresponding parts in each of the several views and wherein:

FIG. 1 is a schematic view of a user's head shown in phantom lines with a hat embodying the present invention in normal position thereon and showing the manner by which direct rays of sunlight penetrate through the cellular visor to certain portions of the wearer's face but with the eyes shaded from such direct rays.

FIG. 2 is a view in side elevation of an embodiment of the invention.

FIG. 3 is the top and/or plan bottom plan view of an embodiment of the invention.

FIG. 4 is a fragmentary top or bottom plan view of the honeycomb visor portion of the hat shown in FIG. 2.

FIG. 5 is a longitudinal sectional view of a modified form of hat construction showing the axes of the honeycomb cells disposed from perpendicular to the plane of the visor.

FIG. 6 is an enlarged fragmentary view of the device shown in FIG. 5.

FIG. 7 is a top or bottom plan view of a second embodiment of the invention.

FIG. 8 is a side elevational view of same.

FIG. 9 is a fragmentary plan view showing in broken lines the resilient lateral movability and adjustability of the rearward extremities of the foam plastic visor portion.

Figure 10:
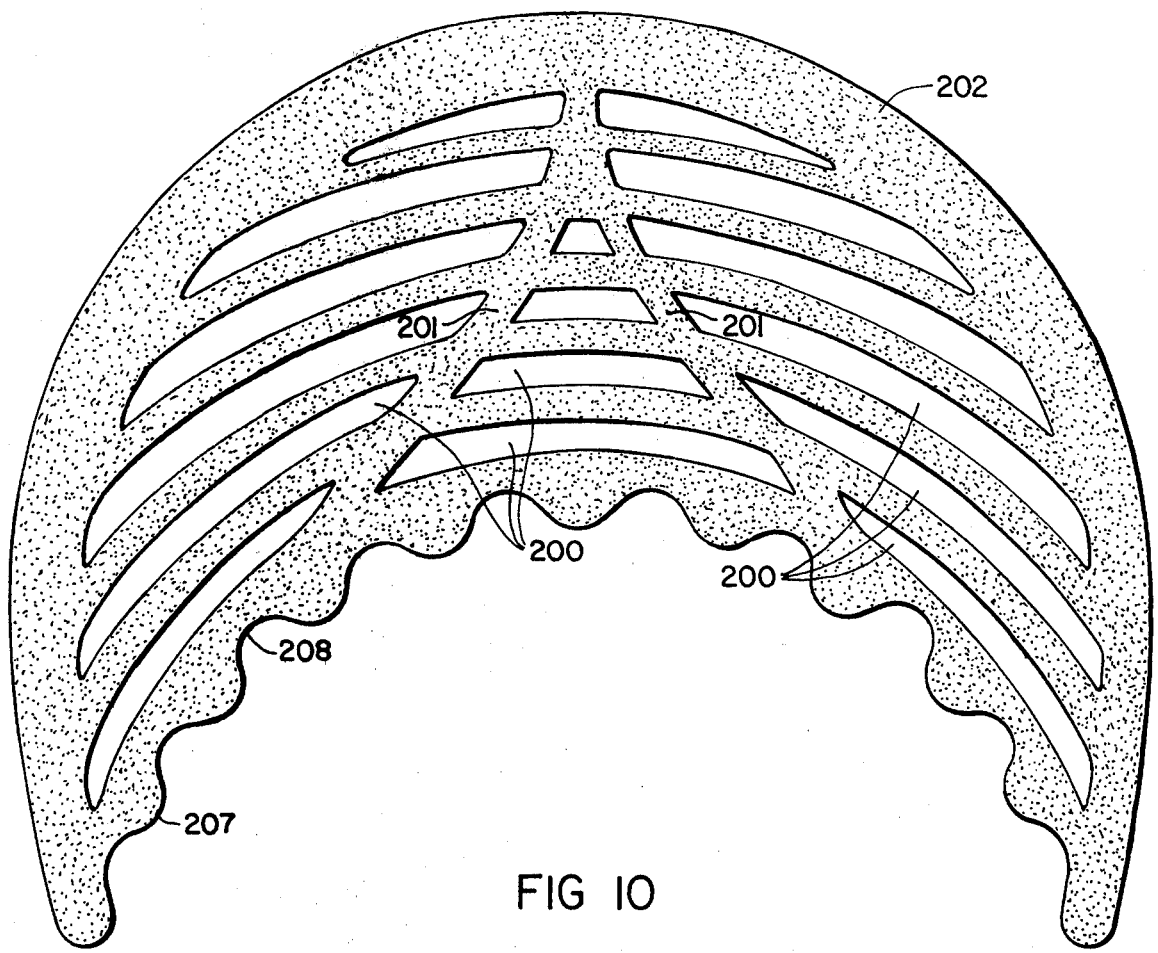
FIG. 10 is a top plan view of a further embodiment of the invention.

Referring now to FIGS. 1–6 of the drawings, the visor portion of the hat is indicated generally at A and the encircling hat band portion thereof is indicated generally at B. FIG. 3 of the drawings shows the construction as comprising a continuous outer hat band 1, an inner hat band 2, a cellular honeycomb visor portion 3 and an inner sinusoidally configured headband 4.

As shown in FIG. 3 the outer hat band 1, defines the outer boundaries or perimeter of the cellular honeycomb visored portion 3 of the hat, and said hat band 1 continues to extend rearwardly from both sides of the visor portion to back of the hat whereat the respective ends 1a and 1b of the hat band overlap to provide a means for making the hat adjustable in size to accommodate varying head sizes. More specifically, as shown in FIG. 3, the terminal extremities 1a and 1b of the headband are divided with coacting, releasable securing means indicated at 6 such as conventional barbed nylon elements commonly referred to as "Velcro" fasteners. One element of the Velcro fastener indicated generally at 6b is adhered to the outer surface of the end extremity 1b of the hatband, whereas the second and coacting part 6a of the Velcro fastener is affixed as by bonding to the inner surface of extremity 1b of the hat. As shown in phantom lines, and in order to adjust the hat to make it of larger or smaller diameter to individually fit a wearer's head, the extremities 1a and 1b and merely pulled apart from each other and, when moved to relative desired longitudinal positioning for the proper head fitting, are simply pressed together whereupon the Velcro fastener will hold the heat at that particular size.

The rearward extremities of the inner sinusoidally curved headband 4 terminate as at 4a and 4b, short of the overlapping end extremities 1a and 1b of the hat band to permit head size adjustment to be made as aforesaid without interference from the inner headband 4. The inner hat band 2 which defines the inner curved periphery of the visor portion 3 is integrally secured as by adhesive bonding at points 2a and 2b to the outer hat band 1. The inner headband 4, in turn, is securely fastened as by bonding to the inner surface of hat band 2, as well as to the inner adjacent surfaces of outer hat band 1.

The honeycomb cellular construction as specifically shown in FIG. 2 comprises alternate bonded layers of corrugated sheet material 3a and planar sheets or strips of sheet material 3b. The nodes of the outer or forwardmost layer of corrugated strips 3a are bonded to adjacent contacting points to the outer hat band 1 and likewise whenever the honeycomb material 3 comes in contact with either outer hat band 1 or with inner hat band 2, the honeycomb is bonded to said hat bands at the contact points to make the entire visor portion 3 an integrally bonded and semi-rigid structure.

The interior headband 4 is preferably formed generally in the form of a corrugated or sinusoidal configuration defining alternate inwardly projecting nodes 7 and grooves 8. The headband is preferably made of a relatively fine cell, substantially non-absorbent, soft textured expanded or foamed plastic material such as a cellular vinyl or polyethylene foam.

When the outer hat band 1 is adjusted to proper size in the manner hereinabove described, the hat, if properly fitted can be worn in substantially horizontal position on the head of the user (substantially as shown in FIG. 1) with only the weight of the hat holding it in position, and with only the spaced nodal points 7 of the interior headband contacting the forehead and other portions of the hair and head of the wearer. As earlier indicated the inherent light weight of the cellular construction of the hat makes it extremely comfortable and also, as above indicated, because of its open cellular visor construction, the hat will not blow off even at relatively high wind velocities.

When properly constructed the hat of the present design and construction should at all times keep the wearer's eyes shaded from direct rays of the sun yet strike lower portions of the user's face to provide for more or less uniform suntanning if that be so desired. In this latter connection it is apparent that the continuous normal motions of the user's head in conjunction with the ever changing angles of the sun rays directed toward and through the cellular visor will operate to varyingly but substantially uniformly distribute the direct sunlight rays over the user's face without leaving a visible and telltale sunburn border around the forehead that is often common to the wearing of conventional opaque visor hats. Further, and in the same connection, because the inner headband 4 is sinusoidally formed leaving the grooves 8 as open spaces between the user's forehead and the headband, such areas of skin are subject to exposure of sun rays which further eliminates or minimizes the non-uniform suntanning of even those portions of the forehead which the headband engages and overlies.

In designing a visored hat embodying the invention in such a way as to provide complete shading of the eyes from direct sunlight rays (indicated at 10 in FIG. 1) while making the visor of substantially open cell construction, there are four primary factors which should be taken into account and correlated to provide the desired objective. The first three factors involve the relationship between the thickness of the visor (the depth or height of the cell openings), the nominal cell and the angle of the axes of the cells to the plane of the visor diameter. The thicker the visor and the smaller the cell openings the greater the light cutoff angle and the greater will be the total area provided under the visor. Conversely, the thinner the visor in terms of height of the cells and the larger the cell openings will result in a larger light cut-off angle and less shade area. Thirdly, by slanting the axes of the cells (as shown in FIG. 5) the light cut-off angle of the sun rays in reference to the thickness of the structure can be varied. Optimally the present hat construction should be designed so that complete shading against direct sunlight rays to the eyes is insured while at the same time making the visor as open celled as light weight as possible. The fourth factor which I have taken into consideration in designing the optimum construction is the fact that within the range of human physical normalcy the eyes within their sockets are disposed inwardly from and are protected and shaded in part by the overhanging brows of the wearer. In short it is possible and desirable to take into account the normal and usual fact that the brows and eyebrows of the normal individual provide to some degree natural sunshade protection. Accordingly, and as indicated in FIG. 1 of the drawings, the angles of sunlight rays show that in the optimum construction the rays may strike the user's brows and also areas immediately below his eyes, but rays do not enter at such a wide or slanted angle as to directly strike the user's eyes themselves.

One example of a basic visor hat incorporating substantially all of the foregoing optimal features herein mentioned was of the following construction.

A sheet of so-called rigid polyvinylchloride of nominal 20 mil thickness was vacuum formed utilizing conventional vacuum forming equipment to form a corrugated sheet which was subsequently sliced into strips 7/16" wide and which said strips were used as the corrugated strips 3a in the drawing. By cutting these strips to desired lengths and by alternatively bonding such strips with flat planar strips of 7/16" wide resin impregnated 80×80 count, 0.0082 cotton cloth 3b, the basic honeycomb visor of the shape shown in FIG. 2 was formed. Thereupon the outer hat band 1, also consisting of a 7/16" strip of 20 mil rigid PVC was bonded to the honeycomb visor portion at substantially all points of contact between the honeycomb and the inner surfaces of the outer hat band 1. Similarly inner hat band 2, which in the instant example consisted of the 7/16" wide resin impregnated cotton strips 2 were bonded at points 2a and 2b to the interior surfaces of the outer hat band 1 as above described.

The inner headband 4 was cut and formed from a larger strip of piece of a fine cell, soft textured vinyl foam material having a manufacturer's specified density of 8–12 lbs/cu.ft. and a 25% compression modulus in the range of 24–40 lbs/cu.ft. This particular material was chosen because of its relatively soft texture and its comfortable "feel" in contact with the skin, and also because of its toughness and apparent durability. Additionally, it does not appear to exhibit any substantial propensity to absorb moisture, or to be subject to unsightly perspiration stain.

The interior hat band so formed was then bonded throughout its exterior surfaces to adjacent contacting surfaces of the inner hat band 2 and the outer hat band 1, as aforesaid.

The coacting parts of the barbed nylon or Velcro fasteners were bonded as heretofore mentioned to the rearwardly extremities 1a and 1b of the hat band 1.

The nominal cell size of each of the honeycomb cells comprising the visor portion 3 of the hat measured 7/16" longitudinally in the direction of x and 7/16" measured transversely in the direction of y as shown more specifically in FIG. 4.

In the foregoing example, all of the materials were bonded to each other by a solvent based (methylethyl ketone) polyurethane room temperature curing resin manufactured by United Shoe Machinery Company. Additionally the planar cotton strips 3b forming part of the honeycomb structure were pre-impregnated with the same polyurethane resin and permitted to dry and at least partially cure so as to be dry to the touch before being placed in the jig and bonded to the corrugated PVC corrugated strips as above stated.

It is also contemplated that the visor portion of the hat may be formed of a honeycomb cellular material with the axes of the cells slanted or angled from perpendicular to the plane of the hat as shown in FIG. 4. More specifically, by slanting the cells so that the cell axes define an obtuse angle "s" (as defined by the angle formed between the upwardly projected axis of a given cell and the plane of the visor measured from a point located forwardly and outwardly from said cell axis), the light cut-off angle from direct sun rays to the eyes and face of a user can be increased, and if desired, the relative thickness of the visor can be thereby reduced and still provide optimum shading and other performance characteristics above mentioned. Honeycomb of a type having its cell axes slanted in reference to the plane of the material is already known and is disclosed in U.S. Pat. No. 3,006,798 for example.

From the foregoing description and as shown in FIGS. 1–6 it will be perceived that the inner and outer hat bands 1 and 2 and the visor portion 3, are all of the same and uniform thickness and width and all of the elements are integrally and structurally secured to one another in substantially flat coplanar relationship to one another. Additionally the interior headband 4 is preferably of the same thickness as the hat bands 1 and 2 and is also disposed in flat coplanar relationship with the other elements comprising the basic visored hat construction herein described. The outer hat band 1 including the rearwardly extending portions thereof which encircle the sides and back of the wearer's head in conjunction with the adjustable fastening means, such as the Velcro type fastener 6, is of sufficient strength and rigidity to provide the necessary support for the outwardly projecting and cantilevered weight of the honeycombed visor so that during normal wear of the hat the visor and hat bands are at all times maintained in their substantially flat coplanar relationship as above stated.

Referring now to FIGS. 7-9 there is disclosed a more advanced and preferred embodiment of the invention which essentially consists of only two parts—an integral visor portion A' (which also integrally defines and provides sinusoidal headband portion 102) and an encircling hat band B' which at its rearward extremities is provided with coacting Velcro or other type or adjustable fasteners 106 of the type heretofore described in reference to the embodiment of FIGS. 1-6.

The visor portion A' is formed of a single integral section of extremely low density, cushiony, relatively non-absorbent, plastic foam material such as for example $\frac{3}{8}''$ thick 2 lbs/cu.ft. density cross-linked polyethylene foam. This section of foam is formed, as by die cutting, with the desired pattern of cell openings or holes to provide a generally honeycomb type structure.

I am presently aware of two commercially available sources of acceptable nominal two to four pound per cubic foot density cross-linked polyethylene foam. One source is manufactured by Voltek, Inc. of Lawrence, Mass. and sold in the United States under the brand name VELORA. Another product sold under the brand name of EVAZOTE manufactured in the United Kingdom (and distributed in the United States by Wilshire Foam Products in Los Angeles and perhaps other distributors) also is a satisfactory candidate material for manufacturing hats embodying the present invention. It is considered within the scope of the invention to make the visor out of either somewhat heavier or lighter foam materials for example within the range of 1 to 6 lbs/cu.ft. density. However, there appears to be no practical advantage in making the visored hat any lighter than can be accomplished with a 2 lbs/cu.ft. density nor is there any foreseeable advantageous reason for adding weight to the hat by using a material of greater density than 2 to 3 lbs/cu.ft. Further, although cross-linked polyethylene foam provides all of the attributes herein mentioned it is within the socpe of the invention to utilize other substantially opaque and non-reflective, soft textured, cushiony, durable and substantially no-water absorbent foams that may presently exist or become available.

In the particular embodiment shown in FIG. 7 the visor section is formed by die cutting a pattern of circular openings as shown of five different sizes although it is understood that the visor might be formed with holes of any geometric shape or design of uniform size or of different sizes as desired. As has been earlier indicated, a visored hat complete with visor and hat band according to this invention can be fabricated to weigh approximately 7 grams or 0.25 of an ounce which is perhaps 5 to 10 times lighter weight than the more popular brands of open top cotton cloth tennis visors in common use today.

It is within the scope of the invention to make the visor of somewhat greater or lesser thickness than $\frac{3}{8}$ of an inch, for example, within the range of not substantially less than $\frac{1}{4}''$ and not substantially greater than $\frac{1}{2}''$ in thickness. The maximum hole or cell size would have to be determined in reference to the selected thickness to provide the proper light cut-off angle and to provide optimum wind resistance. Honeycomb visors providing light cut-off angles within the range of not substantially less than 35° to 60° or more are considered within the known or contemplated practical ranges.

In the embodiment shown in FIG. 7 the hat band B' may be preferably formed of a single layer or laminated strip of fabric or plastic material of the same thickness as the thickness of the visor section A'. The hatband B' may be bonded as by means of a strip of double faced pressure sensitive adhesive 150 to the outer perimeter of the foam visor section A'.

The hat band preferably should be "semi-rigid" in the plane of its width but be quite flexible in the plane normal to its width. More specifically, I have found that the most satisfactory results in terms of fitting and wear is accomplished when the hat band has sufficient structural integrity to support itself in the same plane, or reasonably close to the same plane, as the horizontal visor. On the other hand the hat band should (in the plane normal to its width) be quite flexible so as to bend and conform to the sides and back of a wearer's head when it is adjusted to proper hat size. With the hat band made "semi-rigid" as herein defined, I have found that the visored hat can be more lightly and comfortably adjusted to a user's head than if the hat band is made of a totally flexible material such as a single strip of conventional seamstress ribbon or the like. Furthermore, the hat band should be made of a tough and rugged material that is reasonably tear or permanent crease resistant so that it will not break or become permanently deformed during rough handling of the hat during storage or handling. A hat band having the characteristics of a heavily starched conventional elastic band comes very close to providing all of the desired and optimum hat band characteristics as above mentioned. Further, a band with some degree of elasticity makes the hat band even more adjustable to fit and conform to any normal head size.

The headband portion indicated generally in 104 of visor A' and which is sinusoidal in outline defining alternate nodes and valleys 107 and 108 respectively is of course formed or die cut out of the same integral section of light weight cushiony foam material as defines the entire visor section A. As previously described the visor contacts the user's head only at the spaced points defined by the nodes 107 of the sinusoidal wave. Although a sinusoidal headband as described in FIG. 3 of the first embodiment was provided to substantially completely encircle a wearer's head from front to back, it has been found, especially in connection with the extremely light weight design of the embodiment of FIG. 7 that the sinusoidal headband portion need be only coextensive with the inside perimeter of the visor portion A' to thereby contact virtually only the forehead portion of the user's head.

The sinusoidal headband portion 104 of the visor A' is generally arcuate and in the preferred embodiment defines a slightly elliptical pattern with the dimensions of the two major radiis of curvature being within the approximate range of 3 to 3½" in the direction of line Y—Y and 2½" to 3½" in the direction of line X—X shown in FIG. 7. This configuration appears to satisfactorily fit people of varying head sizes and shapes.

Referring now to FIG. 9 it is seen how each rearward extremity of the visor portion A' as it narrows from forward to rear actually forms or defines a resilient rearward leg or extension (the general vicinity of which is indicated at 160) and which because of the resiliency of the material can move laterally, inwardly or outwardly to the actual distances shown in dotted lines without significantly deforming, twisting, or bending the visor section from its desired substantially planar configuration. This ability of the rearward extremities of the visor section A' to resiliently laterally move inwardly and outwardly provides an additional and somewhat unexpected capability for the hat to adjust itself to head sizes of different widths and shapes without deforming the entire visor from its planar configuration.

In respect of the particular design shown in FIG. 7 an extraordinary functional and aesthetically pleasing visored hat may be formed using ⅜" thick foam material with the five hole sizes progressing upwardly from ¼", 5/6", ⅜", 17/16" to a maximum of approximately ½". This particular pattern has been found to provide adequate light cut-off angles to users who have worn the cap experimentally. In this connection, and again somewhat surprisingly, it has been found that the larger or say ½" holes through a ⅜" thick sheet may not in case of all individuals completely cut off the direct rays of a high overhead sun to the eyes if the wearer holds his head absolutely still and gazes upward. However, from a practical and useful standpoint this fragmentary or partial direct ray penetration appears not to be of practical consequence. It is not known for sure why this is or should be the case but it is believed that because the wearer is generally moving his head to some degree or other and that generally his eyes are looking forward rather than upward, that the occasional "smattering" of direct rays that may not be "cut off" do not create a sufficient physical trauma to the wearer to make him consciously uncomfortable or annoyed by virtue of such effect.

In the embodiment of the invention as particularly described in reference to FIGS. 7-9, the entire hat comprises or consists essentially of only two structural elements—the single and integral open celled sheet of low density cushiony foam material (which defines the entire visor area as well as the sinusoidal cushiony headband portion) in conjunction with a strip or ribbon of substantially the same width as the thickness of the visor (and which is adhesively or otherwise secured to the outer perimeter of the visor and with its rearward extremities of sufficient length to encircle the back of the head of a wearer).

Figure 11:
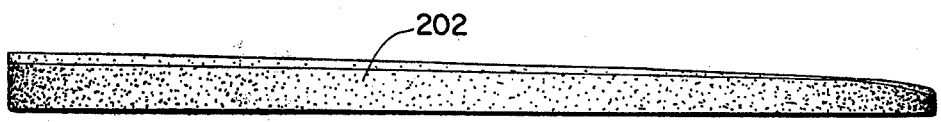
FIG. 11 is a side elevational view of same.

Referring more specifically to FIGS. 10 and 11, there is disclosed a visor section 202 which, like the visor previously described in reference to FIGS. 7-9, can be formed by die cutting openings from a single integral section of low density, cushiony, relatively non-absorbent, plastic foam material, such as for example, ⅜" thick, 2 lb./cub.ft. density, cross-linked polyethylene foam. The openings shown in the visor embodiment of FIGS. 10 and 11, instead of consisting of varying sized circular holes, as previously described with reference to FIGS. 7-9, are arcuate elongate, and indicated generally by the reference numeral 200. The visor in FIGS. 10 and 11 is reinforced and stiffened by one or more beam portions 201, which, if formed by die cutting, as above suggested, would simply consist of uncut portions of the plastic foam material.

FIG. 10 also shows the inclusion of a sinusoidal headband portion formed interval with the visor section and defining alternate nodes and valleys 207 and 208, respectfully.

Embodiment of FIGS. 10 and 11 shows the visor tapered toward outer extremities. For example, if the maximum thickness of the visor is ⅜", it may be tapered outwardly to thickness of around 3/16". Utilizing a maximum thickness of ⅜", the preferred maximum width of each arcuate opening 200, should not exceed the maximum of approximately ½" and preferably somewhat less to provide an adequate light cut-off angle to the eyes of the user.

The visor section of FIGS. 10 and 11 may, like the other embodiments, be utilized as a visor for the conventional cap, or it may be provided with a hat band (not shown) similar in nature to the hat band as shown and described in reference to FIGS. 7-9. If the visor is tapered, as shown in FIGS. 10 and 11, it is apparent that any hat band embracing the outer perimeter of the visor should be correspondingly tapered.

The uniqueness and synergistic functionality of the present invention can be understood by reference to the fact that the combination of a single die cut (or otherwise fabricated) section of a flat section of commercially available cushiony foam material (such as a ⅜" thick section of 2 to 4 lbs/cu.ft. density cross-link polyethylene) in conjunction with a simple hatband ribbon or strip (preferably adjustable) provides a sunshade or visored hat structure which has each and all of the following features and functional attributes:

(1) Extraordinary light weight. A complete visored hat can be fabricated to weigh approximately 6 grams or 0.21 ounces which is 5 to 10 times lighter in weight than the majority of popular open top cotton visored hats of which I am aware. Although the relative comfort or discomfort which any particular individual experiences in wearing any given hat is largely a matter of that individual's subjective judgment, by being able to make a hat of such extremely light weight as the present one, and in conjunction with the features of complete lateral vision, I have observed that the majority of persons who have experimentally worn hats of the specifications herein described become virtually unaware or unconscious of the fact that they are wearing any hat or headwear at all after a certain period of time.

(2) Unobstructed lateral vision. Because the visor portion of the present invention is flat rather than arched, a wearer is permitted unobstructed lateral vision. As above noted, this feature in conjunction with the extreme light weight of the hat gives the unique sense of almost complete freedom from wearing any hat.

(3) Low wind resistance. As already explained, the largely open cell visor offers very little wind resistance especially compared to conventional solid or non-perforated visors.

(4) Perspiration and stain proof. Because the hat is supported at ventilated contact points around the forehead there is no sweat band to either induce or absorb perspiration. There are those individuals who prefer to wear an absorbent sweat band and for those who do, there is nothing inconsistent with the wearing of an absorbent cloth sweat band in conjunction with a hat of the present type being worn around the sweat band. The fact still remains that because the visor, including the sinusoidal headband portion thereof, is made of relatively nonabsorbent foam plastic, the same does not absorb perspiration from the sweat band and further, with or without a sweat band, the hat remains virtually immune to unsightly perspiration stains and odors and is commonly experienced with the more conventional type cloth visored caps which have "built in" sweat bands. Should the material show marks of dirt or stain the same may be washed off with soap and water without, of course, absorbing any appreciable amount of water.

(5) Although the cell configuration of the visor is designed to shade the wearer's eyes from direct sunlight the cells or openings permit filtered rays to be cast on the face of a wearer which provides for gentle sun tanning without leaving a tell-tale sunburn border around a person's forehead which is often observed with people using the usual cloth or opaque visors in conditions of prolonged hot sun exposure.

(6) Hat Size Adjustability. As above indicated the rearward extensions of the hat band are provided with interlocking adjustable fastener means (such as a Velcro type fastener) to enable the hat to be custom fitted to most adult sizes ranging, for example from $6\frac{1}{2}$ to $7\frac{3}{4}$ hat size. However, it is not only the adjustability of the hat band length that permits the hat to comfortably accommodate itself to various head sizes and widths. I have found that by designing the inner sinusoidal headband portion of the visor within the radii of curvatures hereinabove specified the hat seems to fit reasonably uniformly and comfortably persons with both relatively large and small heads. Synergistically, the resiliency of the soft cushiony material from which the visor (including headband) is formed contributes to the hat's ability to accommodate itself to heads of various shapes and widths, but without deforming the visor from its substantially flat or planar configuration. In particular, the rearward extremities of the light weight foam visor can resiliently and laterally move outwardly or inwardly an appreciable amount (See FIG. 9) to accommodate relatively wider and narrower size heads without creating internal stresses in the resilient material of such magnitude as to cause the said lateral extremities to bend or deform from the desired planar configuration.

(7) Structural Integrity and Durability. Another synergistic feature of the embodiment of the invention is that the visored hat provides two features that could even be thought of as inconsistent with one another in the context of more conventional visored hat designs. More specifically, the present visor although being made of a very light weight resilient and cushiony plastic foam, has sufficient integrity and plastic memory to maintain itself in the desired flat or planar configuration during wear. However, when not in wear, it is capable of withstanding very rough handling and abuse without permanently, deforming, wrinkling or rupturing. Most prior art hats of which I have knowledge and which have visors of anywhere near the area of the visor of the present invention are made from reinforced cloth (such as cardboard reinforced cotton visored caps) or from a semi-rigidized plastic material or similar composites. My observations to date have not revealed any conventional reinforced or stiffened visor that is capable of being crushed, wrinkled or twisted to the extent that the light weight foam visor of my invention can be so subjected to, without causing permanent deformity or some other structural or visual damage to the visor portion of the hat.

Although the several embodiments of the invention as shown in the drawings and as above described in some detail are each adapted to function as a basic sunshade to shield the eyes against direct rays or sunlight (or other intense overhead source of light) and all of the attendant features and advantages hereinabove mentioned, it is contemplated that the same basic construction may be utilized in conjunction with manufacturing hats with full or partial crowns of any form or style desired. The crown portions may be bonded or otherwise secured to the basic visored hat unit as herein exemplified. In the event that a crown is utilized in any manner above suggested, the grooves 8 or 108 of the inner headband 4 or 104 will function to provide air ventilation passages opening to the inside of the crown of the hat and again rendering it unnecessary, even in a crowned hat to provide the usual cloth or other moisture absorbent encircling sweat band with its attendant disadvantages hereinabove pointed out.

Although the present invention has been described in some detail by way of illustration and example for purposes of clarification, it is understood that the breadth of the present invention is limited only by the scope of the claims appended hereto.

Having now described the invention, what is claimed is:

1. In a hat construction of the type including an outwardly projecting visor the improvement comprising: head engaging visor support means for supporting the inner extremeties of said visor within the horizontal plane of a user's forehead, whereby said visor projects outwardly from the forehead substantially perpendicular thereto above the normal line of sight of a user, said visor comprising a substantially flat section of relatively low density material and having a thickness of not substantially less than $\frac{1}{4}''$ and not substantially greater than $\frac{5}{8}''$; said section formed generally in an open cell configuration defining a plurality of relatively large cell openings extending through the thickness of the section substantially uniformly distributed throughout a majority of the entire area of the visor section; the size and angular inclination of said cell openings and the thickness of said visor section being related to one another to substantially prohibit transmittal of direct rays of sunlight through the cellular visor to the eyes of a user and to thereby shade the user's eyes from overhead frontally and laterally directed rays of light transmitted through said visor, the said flat section comprising said visor providing substantially unobstructed lateral vision to said user and said open cell configuration thereof providing relatively minimal wind resistance to said visor section; said visor section being formed from an integral section of substantially opaque, cushiony, non-water absorbant, foamed material of not greater than about 6 lbs./cu.ft. density.

2. The combination of claim 1 and wherein said head engaging visor support means is formed as an integral part of said visor section and comprises an integral headband portion; and wherein said headband portion consists of pre-selected portions of said foamed material defining the interior perimeter of said visor section for engaging the forehead of a user only at spaced contact points.

3. The combination of claim 2 and wherein said headband portion of said integral visor section of foamed material is formed generally in a concave arcuate configuration to fit the forehead of a user, and wherein said arcuate headband defines an undulating wave band of alternate nodes and grooves whereby said headband contacts the forehead of said user only at said spaced nodal points of said headband.

4. In a hat construction of a type including an outwardly projecting visor portion, the improvement comprising said visor formed generally in an open cell configuration; said visor comprising a section of predetermined substantial thickness and defining a plurality of cell openings extending through the thickness of said section and being substantially uniformly distributed throughout the majority of the entire area of the visor section; said visor section being substantially planar throughout its entire area; said visor section being formed of semi-rigid material and having sufficient structural strength and integrity to maintain itself in said substantially planar form during normal wear; the thickness of the visor section and nominal cell size of the honeycomb cells being related to provide an overhead light cut-off angle of sufficient degree to substantially prevent penetration of direct overhead frontal and lateral light rays through the honeycomb visor to the eyes of a user when said hat is worn on a user's head with the plane of the visor in substantially horizontal position; a headband for at least partially encircling and engaging the head including the forehead of a wearer and being made from the same piece of material as said honeycomb visor section and extending rearwardly thereof in substantially the same plane as said visor section; said headband formed of relatively soft textured, non-absorbent foam material with its inner surfaces defining alternative inwardly extending nodal points and intervening grooves therebetween, whereby when said headband is fitted to a user's head only said nodal points of the headband contact the adjacent positions of a said user's head.

5. The combination of claim 4 and wherein the combined area of the nodel contact points is much less than the ventilated non-contact areas defined by the grooves between said nodal contact points.

6. An article of unique headwear comprising a sun visor adapted to be operatively worn in a position projecting frontally and substantially perpendicular to the surface of the user's forehead above eye level and within the horizontal plane of a said user's forehead; said visor formed of an integral section of substantially opaque, light weight, soft textured, non-water absorbant cushiony material having an average minimum thickness of not substantially less than $\frac{1}{4}''$ and not substantially greater than $\frac{3}{4}''$; said visor section formed throughout the majority of its surface area with a plurality of spaced openings extending through the thickness of said section; the maximum cross section of the largest of the openings being related to the thickness of the section in which said opening is formed to provide an overhead frontal light cut-off angle of not substantially less than 60°; thus, substantially preventing transmittal of direct rays of sunlight through the visor to the eyes of a user.

7. The combination of claim 6 and wherein the nominal density of said foam visor is within the range of about 1 to 6 lbs./cu.ft.

8. The combination of claim 6 and wherein the nominal density of said foam visor is in the range of about 2 to 4 lbs./cu.ft.

9. In a hat construction of the described type, a visor formed of non-water-absorbing material outwardly projecting from the main hat body as a substantially flat surface perpendicularly from the surface of the wearer's forehead above eye level and within the horizontal plane of said wearer's forehead, said visor being formed of a section of relatively low density non-water-absorbing material having a thickness in the range between approximately $\frac{1}{4}''$ and $\frac{5}{8}''$, the said section being formed with a plurality of relatively large openings extending through the thickness of the section throughout a majority of the entire area of the visor section, the size and angular inclination of said cell openings and the thickness of said visor section being related to one another to substantially prohibit transmittal of direct rays of sunlight through the cellular visor to the eyes of a user and to thereby shade the user's eyes from overhead rays of light transmitted through said visor, the said flat section comprising said visor providing substantially unobstructed lateral vision to said user and said open cell configuration thereof providing relatively minimal wind resistance to said visor section; the cell openings of said visor section being substantially arcuate elongate in plan with the arcuate length of the cells extending generally parallel to and in the same arcuate path as the arcuate periphery of the visor section.

* * * * *